United States Patent [19]

Kingston et al.

[11] Patent Number: 5,296,506
[45] Date of Patent: Mar. 22, 1994

[54] REARRANGED TAXOL COMPOUNDS AND METHOD OF USING IN TESTING OF IN VIVO ACTIVITY

[75] Inventors: David G. I. Kingston; Gamini Samaranyake, both of Blacksburg, Va.

[73] Assignee: Virginia Tech Intellectual Properties, Inc., Blacksburg, Va.

[21] Appl. No.: 978,713

[22] Filed: Nov. 19, 1992

Related U.S. Application Data

[60] Division of Ser. No. 839,082, Feb. 24, 1992, Pat. No. 5,194,635, which is a continuation of Ser. No. 670,432, Mar. 18, 1991, abandoned.

[51] Int. Cl.$^5$ .................. A01N 43/02; C07D 305/00; C07D 407/00
[52] U.S. Cl. .................. 514/449; 549/214; 549/510; 549/511
[58] Field of Search ............. 549/510, 511; 514/449

[56] References Cited

U.S. PATENT DOCUMENTS 5,194,635  3/1993  Kingston et al. .................. 549/410

FOREIGN PATENT DOCUMENTS 0336841  10/1989  European Pat. Off. ............. 549/510

OTHER PUBLICATIONS

Tetrahedron Letters, vol. 33, No. 51, pp. 7915-7916, 1992, "*Taxchinin A: A Diterpenoid From Taxus Chinensis*".
Tetrahedron vol. 48, No. 34, pp. 6965-6974, 1992, "*Rearrangement Reactions of Taxanes: Structural Modifications of 10–Deacetylbaccatin III*".
Magri et al., *J. Org. Chem.*, 1986; 51 pp. 797-802.
Huang, *J. Nat. Prod.*, vol. 49, No. 4, pp. 665-669, Jul.-Aug. 1986.
McLaughlin et al., *J. Nat. Prod.*, vol. 44, No. 3, p. 312-319, May-Jun. 1981.
Kingston et al., *J. Nat. Prod.*, vol. 53, No. 1, pp. 1-12, Jan.-Feb., 1990.
Chan et al., *Chemical Communications*, No. 24, pp. 923-925, 1966.
Fransworth, Norman, letter to *J. Pharm. Sci.*, IV (1977).

*Primary Examiner*—C. Warren Ivy
*Assistant Examiner*—Raymond Covington
*Attorney, Agent, or Firm*—Mason, Fenwick & Lawrence

[57] ABSTRACT

In a preferred embodiment, taxol is treated with mesyl chloride to prepare a taxol derivative with a contracted A-ring, which has comparable activity to taxol in a tubulin depolymerization assay, and which shows cytotoxicity against KB cells in a cell culture assay. In an alternate preferred embodiment, taxol is treated with triethyloxonium tetrafluoroborate (Meerwein's reagent) to produce a taxol derivative with an opened oxetane ring. In another alternate preferred embodiment, reaction of taxol with acetyl chloride yields a taxol derivative in which the oxetane ring is opened and the A-ring is contracted. All of the aforementioned products show in vivo activity in KB cell culture assays. Further, the preferred compounds have different in vivo activities, which makes them ideal to form a range of standards for use in biological testing of other compounds.

3 Claims, 4 Drawing Sheets

REARRANGED TAXOL COMPOUNDS AND METHOD OF USING IN TESTING OF IN VIVO ACTIVITY

This application is a division of U.S. patent application Ser. No. 07/839,082, filed Feb. 24, 1992, now U.S. Pat. No. 5,194,635 which is a continuation of Ser. No. 07/670,432 filed Mar. 18, 1991 abandoned.

FIELD OF THE INVENTION

This application is directed to rearranged taxol compounds, and more particularly is directed to taxol derivatives with an opened oxetane ring, taxol derivatives in which the oxetane ring is opened and the A-ring is contracted, and taxol derivatives with a contracted A-ring.

BACKGROUND OF THE INVENTION

The naturally occurring diterpenoid taxol has great potential as an anti-cancer drug, and has shown activity in several tumor systems. Background information on taxol, the mechanisms of taxol's biological activity, and the synthesis of water soluble derivatives from taxol, are described in co-pending application Ser. No. 07/573,731, filed Aug. 28, 1990. All references cited herein are incorporated by reference as if reproduced in full below.

Taxol is in short supply and is relatively expensive. Further, total synthesis of taxol is quite difficult due to the bridged bicyclic portion of the taxane ring structure. Therefore, it is highly desirable to find taxol derivatives with similar biological activities, which lend themselves to easier total synthesis than taxol.

There is also a need for a method to quickly determine the biological activities of new compounds or pharmaceutical compounds having bioactivities or structures similar to taxol. The short supply and expense of taxol makes impractical the use of taxol as a standard in determining the bioactivities of other compounds; thus, it is highly desirable that a range of other standards with known biological activities be available to determine the bioactivity of taxol derivatives and other compounds relative to taxol. Useful standards should be derivatives of taxol, or the standards should be compounds which have similar structures to taxol, but which are more readily available or which can be synthesized easier than taxol. At present, some derivatives, which do not exhibit the same high biological activity as taxol, are thrown away; this waste would be eliminated by a method which uses taxol derivatives, which have significantly less biological activity than taxol, as standards in bioactivity testing, rather than utilizing more taxol, which is already in short supply and very expensive.

Thus, there is a need for taxol derivatives having a range of in vivo and in vitro activities, and there is a need for taxol derivatives or compounds having similar biological activities to taxol which are capable of easier total synthesis than taxol.

OBJECTS OF THE INVENTION

Thus, it is a primary object of the present invention to synthesize taxol derivatives having varying in vitro and in vivo activities for use as standards in determining the bioactivity of other compounds in comparison to taxol.

It is a further object of the present invention to synthesize derivatives of taxol, having similar in vivo activities, which are capable of easier total synthesis than taxol.

SUMMARY OF THE INVENTION

These and other objects of the present invention are accomplished through synthesis of compounds useful for the aforementioned purposes and objectives. In a preferred embodiment, taxol is treated with mesyl chloride to prepare a taxol derivative with a contracted A-ring, which has comparable activity to taxol in a tubulin depolymerization assay, and which shows cytotoxicity against KB cells in a cell culture assay. In an alternate preferred embodiment, taxol is treated with triethyloxonium tetrafluoroborate (Meerwein's reagent) to produce a taxol derivative with an opened oxetane ring. In another alternate preferred embodiment, reaction of taxol with acetyl chloride yields a taxol derivative in which the oxetane ring is opened and the A-ring is contracted. All of the aforementioned products show in vivo activity in KB cell culture assays. Further, the preferred compounds have different in vivo activities, which makes them ideal to form a range of standards for biological testing of other compounds.

DETAILED DESCRIPTION OF THE PREFERRED EMBODIMENTS

Figure 1:
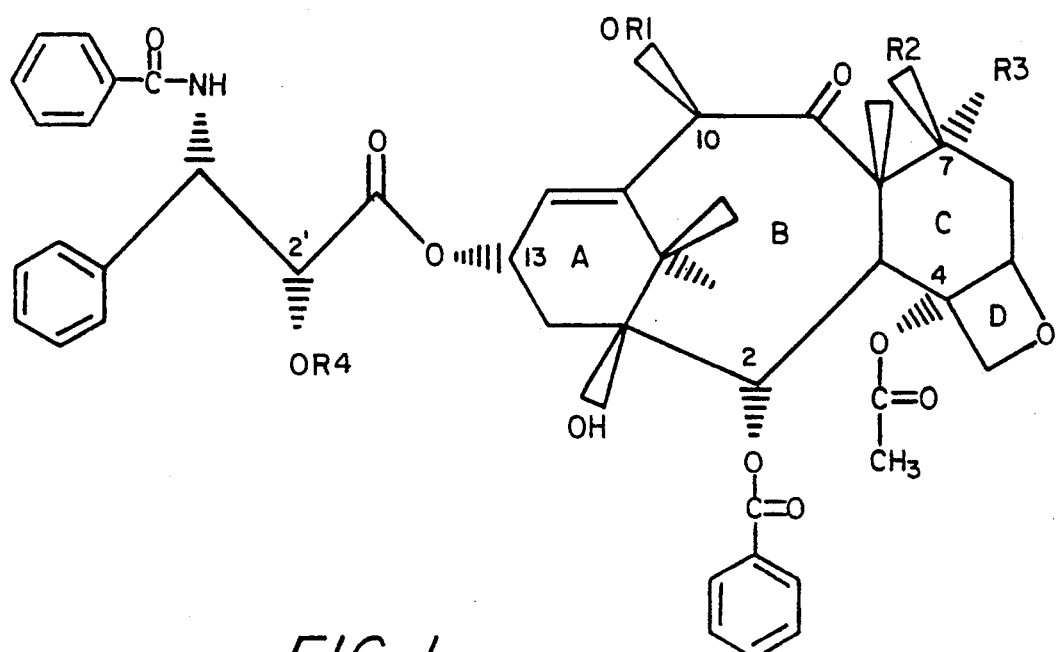
FIG. 1 is a generalized representation of a taxol compound structure.
Figure 2:
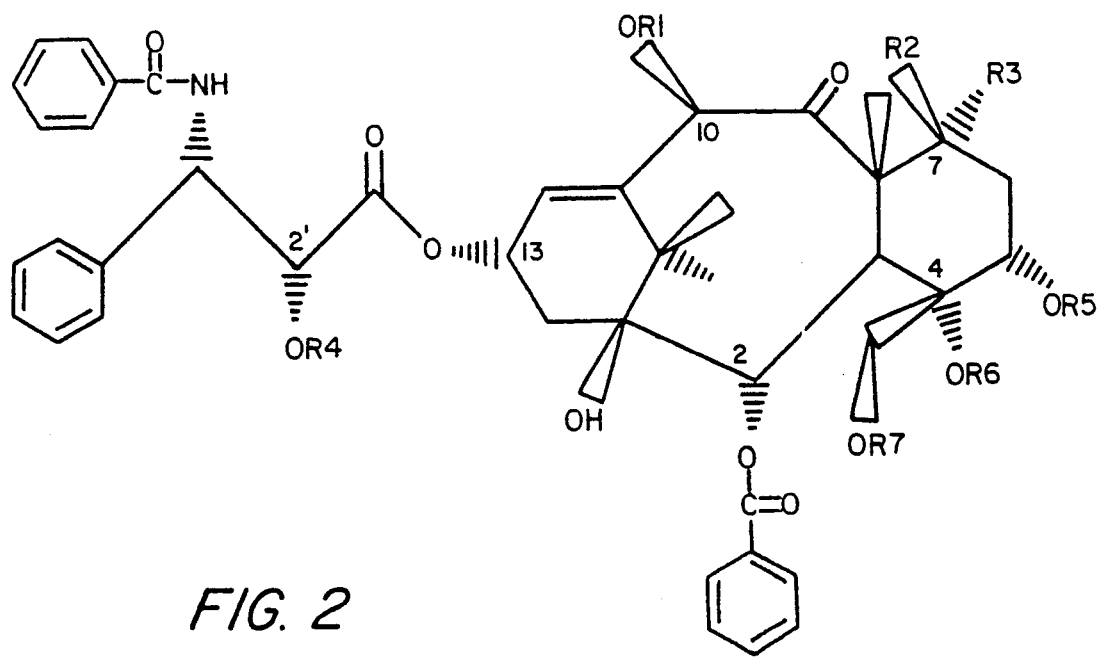
FIG. 2 is a generalized representation of a taxol compound with an opened oxetane ring.
Figure 3:
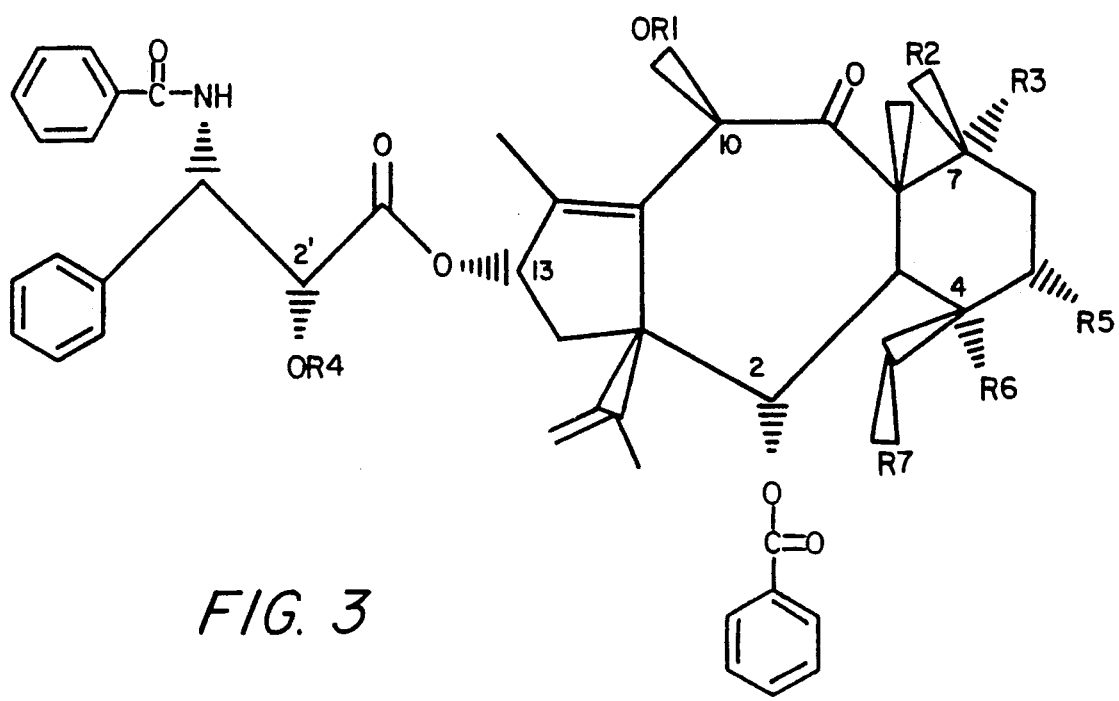
FIG. 3 is a generalized representation of a taxol compound having a contracted A-ring and an opened oxetane ring.
Figure 4:
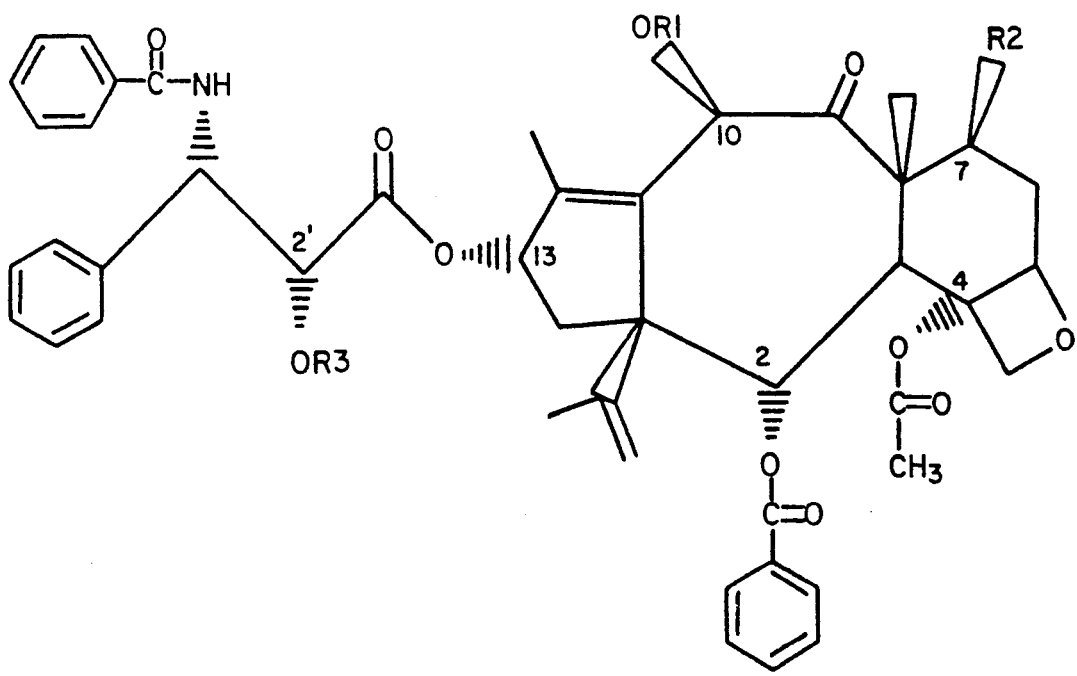
FIG. 4 is a generalized representation of a taxol compound with a contracted A-ring.

With reference to FIG. 1, the structure of taxol (1) is represented when R1 is $C(O)CH_3$, R2 is OH, R3 is H, and R4 is H. The derivatives of taxol discussed herein are represented in FIGS. 1–7, with specific structure variables, R1–R7, defined in Table I below. For the sake of convenience, structures will be referred to by the structure numbers provided in Table I.

TABLE I

| \multicolumn{3}{c}{Variable Definitions For Structures Discussed Herein and Illustrated In FIGS. 1–7} |
|---|---|---|
| Structure Number | Figure Number | Variable Definitions |
| (1) | 1 | R1 = $C(O)CH_3$, R2 = OH, R3 = H, R4 = H |
| (2) | 1 | R1 = $C(O)CH_3$, R2 = H, R3 = OH, R4 = H |
| (3) | 1 | R1 = H, R2 = H, R3 = OH, R4 = H |
| (4) | 2 | R1 = $C(O)CH_3$, R2 = OH, R3 = H, R4 = H, R5 = H, R6 = H, R7 = $C(O)CH_3$ |
| (5) | 2 | R1 = $C(O)CH_3$, R2 = $OC(O)CH_3$, R3 = H, R4 = $C(O)CH_3$, R5 = H, R6 = H, R7 = $C(O)CH_3$ |
| (6) | 2 | R1 = $C(O)CH_3$, R2 = $OC(O)CH_3$, R3 = H, R4 = $C(O)CH_3$, R5 = $C(O)CH_3$, R6 = H, R7 = $C(O)CH_3$ |

TABLE I-continued

Variable Definitions For Structures Discussed Herein and Illustrated In FIGS. 1-7

| Structure Number | Figure Number | Variable Definitions |
|---|---|---|
| (7) | 3 | $R1 = C(O)CH_3$, $R2 = OC(O)CH_3$, $R3 = H$, $R4 = C(O)CH_3$, $R5 = OC(O)CH_3$, $R6 = OH$, $R7 = OC(O)CH_3$ |
| (8) | 7 | $R1 = C(O)CH_3$, $R2 = OC(O)CH_3$, $R3 = H$, $R4 = C(O)CH_3$, $R5 = OC(O)CH_3$, $R6 = OH$, $R7 = OC(O)CH_3$ |
| (9) | 4 | $R1 = C(O)CH_3$, $R2 = OSi(CH_2CH_3)_3$, $R3 = Si(CH_2CH_3)_3$ |
| (10) | 4 | $R1 = C(O)CH_3$, $R2 = OH$, $R3 = H$ |
| (11) | 6 | $R1 = C(O)CH_3$, $R2 = OSi(CH_2CH_3)_3$, $R3 = OH$, $R4 = Si(CH_2CH_3)_3$ |
| (12) | 5 | $R1 = C(O)CH_3$, $R2 = C(O)CH_3$ |
| (13) | 6 | $R1 = C(O)CH_3$, $R2 = OSi(CH_2CH_3)_3$, $R3 = OSO_2CH_3$, $R4 = Si(CH_2CH_3)_3$ |

Due to the complexity of the taxol structure, incomplete understanding of the relationship between the taxol structure and its activity, it was difficult or impossible to predict how derivatives of taxol would behave; further, the complexity of the taxol structure made prediction of reaction product structures equally difficult. The present invention overcomes these problems through the synthesis of taxol derivatives with a contracted A-ring (FIG. 4), with a contracted A-ring and an opened oxetane ring (FIG. 3), or with an opened oxetane ring (FIG. 2), which retain in vivo activity, although at different levels than taxol.

The taxol derivative having a contracted A-ring structure, otherwise known in a preferred embodiment as A-Nortaxol (10), is easier to perform total synthesis of than taxol since the bridged bi-cyclic portion of the diterpenoid structure has been fused. Further, it has been discovered that A-Nortaxol has an in vitro activity very close to that of taxol in a tubulin depolymerization assay. Thus, A-Nortaxol (10) can be used in a similar fashion to taxol (1).

It is believed that the oxetane ring (the D-ring in taxol (1)) is susceptible to ring-opening by reaction with electrophilic reagents, so initial experiments were performed using zinc bromide as an electrophile to attempt to open the oxetane ring on taxol. Taxol (1) was combined with zinc bromide in methanol at ambient temperature, but the oxetane ring was not opened, and the taxol simply underwent epimerization of the C-7 hydroxyl group and cleavage of the 10-acetyl group to yield 7-epitaxol (2) and 10-deacetyl-7-epitaxol (3).

The relatively mild conditions created by zinc bromide in methanol were selected because it was believed that the more vigorous conditions created by other electrophiles and other solvents may result in taxol derivatives without any substantial biological activity due to destruction of part or all of the bioactive portions of the molecule. However, it was surprisingly discovered that treatment of taxol with different electrophilic groups resulted in rearrangement of different portions of the taxol structure, and that some of the various products retained in vivo activity. More specifically, reaction of taxol with the strong electrophile triethyloxonium tetrafluoroborate (Meerwein's reagent) resulted in a taxol derivative (4) with an opened oxetane ring. Reaction of taxol with acetyl chloride yielded a product (7) in which the oxetane ring was opened, but the A-ring was contracted. Treatment of the protected taxol (11) with mesyl chloride, followed by deprotection, resulted in a taxol derivative with a contracted A-ring alone, A-Nortaxol (10).

It was also surprisingly discovered that these rearranged taxol derivatives (4), (7), and (10) all retain varying degrees of in vivo activity, as determined by KB cell culture assays. A-Nortaxol (10) also showed very similar activity to taxol in a tubulin depolymerization assay, and showed higher in vivo activity than the acetyl chloride product (7) and the Meerwein product (4). Thus, the range of activity shown by the taxol derivatives of the present invention make them ideal for use as standards in biological testing. Further, A-nortaxol (10) and the acetyl chloride product (7) are easier to perform synthesis on than taxol since the A and B rings are fused in the products rather than bridged (note that the bridge bond between A and B rings in taxol is extremely difficult to synthesize). Thus, the present invention includes a method, which is highly useful to researchers in determining the activity of compounds in comparison to taxol (1) and taxol derivatives; the method has an additional advantage, since it is not necessary to use the limited and expensive supply of taxol as a control or standard.

In a preferred process, new compounds or production line pharmaceutical compounds, which must be tested to ensure bioactivity in comparison to taxol, are subjected to bioactivity evaluation in parallel with standards utilizing compounds (4), (7), and (10). Since the relative bioactivities of products (4), (7), and (10) are known (in comparison to one another as well as to taxol), the relative bioactivity of the compound being tested to taxol can be determined in a reliable fashion. Thus, in addition to the in vivo activity of compounds (4), (7), and (10), which makes the compounds useful as cytotoxic agents, they are also useful in extending the limited supply of taxol. This is because the Method of the present invention replaces taxol with new compounds in testing other compounds which are used as cytotoxic agents in general, or, which are used as anticancer or anti-leukemic drugs in humans.

METHODS AND MATERIALS

Specific reaction methods are described in more detail in the following non-limiting examples. The methods used herein are generally described in the *Journal Of Organic Chemistry*, 51, pp. 797-802 (1986). Low resolution mass spectrometry data were obtained on a VG 7070 E-HF mass spectrometer. Exact mass measurements were performed at the Midwest Center for Mass Spectrometry, NSF Regional Instrumentation Facility (Grant Che8211164). The term "standard work-up" in the following non-limiting examples includes extraction with a suitable solvent (usually ethyl acetate or methylene chloride), washing the extract with water, drying over magnesium sulfate or sodium sulfate, and evaporation in vacuo. All technical and scientific terms used herein have the same meaning as commonly understood by one of ordinary skill in the art. Other methods and materials similar or equivalent to those described herein can be used in the practice or testing of the present invention.

EXAMPLE 1

Taxol (1) was reacted with zinc bromide, ZnBr as follows: 100 mg taxol (0.117 mmol) was combined with 3.3 g $ZnBr_2$ (0.41 mmol) in 10 ml $CHCl_3$:MeOH(1:4) and stirred for 24 hours at 40° C. Water was added to the mixture, and the standard work-up (as defined above in "Methods") yielded a white solid. The solid was purified by chromatography to obtain two compounds, which were identified as 7-epi-taxol (2) and 10-deacetyl-7-epitaxol (3) by comparison to published data (see *Journal of Natural Products*, 49, pp. 665–669 (1986), and *Journal of Natural Products*, 44, pp. 312–319 (1981); compounds (2) and (3) have been previously described by McLaughlin et al. in *Journal of Natural Products*, 44, pp. 312–319 (1981). Thus, it was necessary to try more vigorous reaction conditions to open the oxetane ring, despite the risk that the more vigorous conditions would cause other portions of the taxol structure to be altered to an extent that the resulting compound would lack any substantial bioactivity.

EXAMPLE 2

Taxol (1) was reacted with Meerwein's reagent as follows: A solution of taxol in dichloromethane was prepared by adding 100 ml taxol (0.117 mmol) to dry dichloromethane. The taxol solution in dichloromethane was cooled and stirred while 200 μl triethyloxonium tetrafluoroborate (1M in $CH_2Cl_2$) was added drop-wise from a freshly opened bottle. These conditions were maintained for 30 minutes, at which time the reaction was quenched with 3 ml of ethereal HCl (1:2 mixture of iN HCl:ether) followed by stirring for 10 minutes. Standard workup gave a crude solid, which was further purified by flash chromotography and PTLC to yield 53 mg (51%) of a taxol compound with an opened oxetane ring (4) (The "Meerwein product"). NMR, MS, and IR (KBr) were performed on a sample of the Meerwein product (4) and its melting point was determined, with the characterization data and NMR data presented in Tables II and III below:

TABLE II

| Characterization Data For Product (4) (Resulting From Reaction Of Taxol With Meerwein's Reagent) | |
|---|---|
| Melting Point | 160–164° C. (amorphous solid) |
| IR (KBr) $cm^{-1}$ | 1745(s), 1670(m), 1535(w), 1505(w), 1474(w), 1395(m), 1120(m), 1080(m), 1060(m) |
| MS(FAB) m/z | 872 ($MH^+$, 100), 854 ($MH^+$, $H_2O$) |
| High-resolution mass spectrum | calculated ($MH^+$) 872.3493; observed 872.3463 |

TABLE III

NMR Data For Reaction Product Of Taxol With Meerwein's Reagent, $C_{47}H_{54}NO_{15}$ (4)

| Carbon Position | $^1$H Shift (PPM from TMS) Coupling Hertz |
|---|---|
| 2 | 5.56 (d,6) |
| 3 | 4.03 (3,6) |
| 5 | 3.70 (br s) |
| 6 | a |
| 7 | 4.49 (dd 4,11) |
| 10 | 6.57 (s) |
| 13 | 6.01 (br dd, 4,11) |
| 14 | 2.45 (dd, 11,16) |
|  | 3.08 (dd, 4,16) |
| 15 |  |
| 16 | 1.12 (s) |
| 17 | 1.12 (s) |
| 18 | 2.10 (s)$^b$ |
| 19 | 1.22 (s) |
| 20 | 3.85 (ABq, 11 $V_{AB}$ = 86) |
| 2' | 4.70 (br s) |
| 3' | 5.92 (dd,2,9) |
| NH | 7.19 (br d,9) |
| OAc | 1.65 (s) |

TABLE III-continued

NMR Data For Reaction Product Of Taxol With Meerwein's Reagent, $C_{47}H_{54}NO_{15}$ (4)

| Carbon Position | $^1$H Shift (PPM from TMS) Coupling Hertz |
|---|---|
|  | 2.25 (s) |
| 2-OBz | 8.03 (m) |
|  | 7.3–7.6 (m)$^c$ |
| 3'-NBz | 8.03 (m) |
|  | 7.3–7.6 (m)$^c$ |
| 3'-Ph | 7.3–7.6 (m)$^c$ |
| OH | 3.91 (s) |

$^a$peak concealed under signals from methyl group
$^b$determined by decoupling experiment
$^c$overlapping peaks

EXAMPLE 3

The Meerwein product (4) was acetylated as follows: 5 mg of the Meerwein product (4) (0.0057 mmol) was dissolved in 100 μl of pyridine, and 300 μl of acetyl chloride (excess) was added to the solution; the solution was kept at room temperature for 30 minutes, and warmed to 60° C. for one hour, followed by quenching with water. Standard work-up yielded crude material which was purified on PTLC to yield 3 mg (55%) of chromatographically homogeneous 2',7-diacetyl-D-seco-taxol (5). Structure was confirmed with $^1$H NMR.

EXAMPLE 4

2',7-diacetyl-D-seco-taxol (5) was acetylated as follows: 8 mg 2',7-diacetyl-D-seco-taxol (5) (0.008 mmol) was dissolved in 750 μl tetrahydrofuran (THF) and to this solution dicyclohexylcarbodiimide (5 mg, 2.5 eq) 4 μl acidic anhydride (5 eq) and a catalytic amount of pyrrolidino pyridine were added. The stirred solution was heated to 60° C. for 7.5 hours, the solvent was then evaporated and the residue extracted into ethyl acetate. Standard work-up yielded a crude mixture which was purified by PTLC with 1% MeOH/$CHCl_3$ to yield 3 mg (38% yield at 63% conversion) of 2',5,7-triacetyl-D-seco-taxol (6). Characterization data is presented in Table IV and NMR data is presented in Table V below.

TABLE IV

| Characterization Data For 2', 5, 7-Triacetyl-D-Seco-Taxol (6) | |
|---|---|
| IR $cm^{-1}$ | 1740(s), 1720(s), 1676(m), 1625(s), 1225(s) |
| MS(FAB)m/z (relative intensity) | 998($MH^+$, 13) 980($MH^+$, 12) 936(6) 848(23), 650(100). |

TABLE V

NMR Data For 2', 5, 7-Triacetyl-D-Seco-Taxol (6)

| Carbon Position | $^1$H Shift (PPM from TMS) Coupling Hertz |
|---|---|
| 2 | 5.63 (d,5) |
| 3 | 4.04 (d,5) |
| 5 | 5.26 (m)$^c$ |
| 6 | a |
| 7 | 5.43 (br d, 9) |
| 10 | 6.42 (s) |
| 13 | 6.03 (m) |
| 14 | 2.40 (dd, 9,15) |
|  | 3.07 (dd, 5,15) |
| 15 |  |
| 16 | 1.13 (s) |
| 17 | 1.11 (s) |
| 18 | 2.24 (s) |
| 19 | 1.38 (s) |
| 20 | 4.01 (ABq, 12 |

TABLE V-continued

NMR Data For 2', 5, 7-Triacetyl-D-Seco-Taxol (6)

| Carbon Position | $^1$H Shift (PPM from TMS) Coupling Hertz |
|---|---|
|  | $V_{AB} = 57$) |
| 2' | 5.26 (m)$^c$ |
| 3' | 6.12 (dd,3,10) |
| NH | 7.20 (br d,9) |
| OAc | 1.98 (s), 2.13 (s), 2.16 (s), 2.19 (s), 2.20 (s) |
| 2-OBz | 8.20 (m) |
| 3'-NBz | 7.8 (m) |
| 3'-Ph | 7.2–7.6 (m)$^c$ |
| OH |  |

$^a$peak concealed under signals from methyl group
$^b$determined by decoupling experiment
$^c$overlapping peaks

EXAMPLE 5

Figure 5:
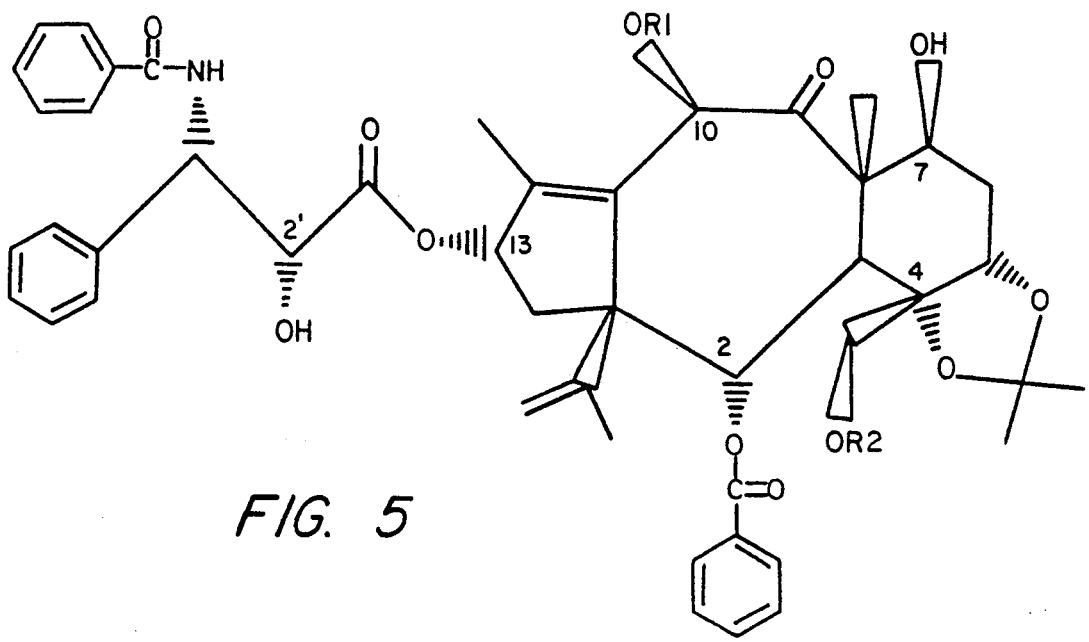
FIG. 5 is a representation of structure of an acetonide of taxol.

The Meerwein product (4) was then treated with 2,2-dimethoxypropane as follows: 6 mg of the Meerwein product (4) (0.007 mmol) and 200 μl 2,2-dimethoxypropane was combined in 500 μl dry dichloromethane along with a catalytic amount of p-toluenesulfonic acid, and stirred for one hour. Standard workup yielded a cruproduct, which was further purified by PTLC to obtain 6 mg (954) of pure acetonide (12) (FIG. 5). The structure of the acetonide (12) was confirmed by $^1$H NMR and by mass spectrometry; MS(FAB) m/z (relative intensity) 916 (MNa+, 100), 855 (MNa+—HOAc—H, 25), 832 (MNa+—CH$_3$Co—C$_3$H$_5$, 50), 761(40). $^1$H NMR data is presented in Table VI below.

TABLE VI

NMR Data For Acetonide (12) Of The Meerwein Product (4)

| Position | $^1$H Shift (PPM from TMS) Coupling Hertz |
|---|---|
| 2 | 5.34 (d,8) |
| 3 | 3.06 (d,8) |
| 5 | 4.34 (m) |
| 6 | $6_{ax}$1.95 (ddd 5, 11, 15)$^b$ $6_{eq}$ 2.36 (ddd) 2,5,15) |
| 7 | 4.48 (dd,5,11) |
| 10 | 6.38 (d,2) |
| 13 | 5.68 (d,2) |
| 14 | 2.57 (AB part of ABX. 9, 14 $V_{AB} = 62$) |
| 15 |  |
| 16 | 4.67 (s), 4.75 (s) |
| 17 | 1.63 (s) |
| 18 | 1.67 (s)$^b$ |
| 19 | 1.62 (s) |
| 20 | 4.15 (ABq, 12, $V_{AB} = 26$) |
| 2' | 4.50 (d,3) |
| 3' | 5.60 (dd,3,8) |
| NH | 6.98 (br d,8) |
| OAc | 1.83 (s), 2.17 (s) |
| 2-OBz | 8.10 (m) 7.3–7.4 (m)$^c$ |
| 3'- NBz | 7.73 (m) 7.3–7.4 (m)$^c$ |
| 3'-Ph | 7.3–7.4 (m)$^c$ |
| OH |  |
| Other | 1.30 (s)$^d$ 1.33 (s) |

$^a$peak concealed under signals from methyl group
$^b$determined by decoupling experiment
$^c$overlapping peaks
$^d$signals of the methyl groups of the acetonide

EXAMPLE 6

Taxol (1) was reacted with acetyl chloride under the following conditions: 200 mg taxol (0.23 mmol) was dissolved in 2 ml acetyl chloride, and the solution was refluxed for one hour. The reaction was quenched with ice water and ethyl acetate, and stirred for 30 minutes. Standard work-up yielded a white solid. Recrystallization of the white solid from ethyl acetate and hexanes yielded acetylated A-Nor-D-seco-taxol (7) (See FIG. 3) as white needles (156 mg, 68%). Characterization data for acetylated A-Nor-D-seco-taxol (7) is provide in Table VII and NMR data is provided in Table VIII below.

TABLE VII

Characterization Data For Acetylated A-Nor-D-seco-taxol (7)

| | |
|---|---|
| Melting Point | 140–142° C. |
| IR(CHCl$_3$) cm$^{-1}$ | 1750 (s), 1660(m), 1606(m), 1372(m), 1282(m), 1156(m) |
| MS(FAB)m/z | 1002(MNa+, 35), 676(MNa+-side-chain, 15), 616(675-HOAc, 30), 554(676-PhCOOH, 20), 494(616-PhCOOH, 30), 411(24), 3722(4), 177(100) |
| High resolution mass spectrum | calculated for C$_{53}$H$_{57}$NO$_{17}$Na(MNa+) = 1002.3524; observed 1002.3557 |

TABLE VIII

NMR Data For Acetylated A-Nor-D-seco-taxol (7)

| Carbon Position | $^1$H Shift (PPM from TMS) Coupling Hertz |
|---|---|
| 2 | 5.35 (d,7) |
| 3 | 3.54 (d,7) |
| 5 | 5.28 (br s) |
| 6 | a |
| 7 | 5.54 (dd,4,13) |
| 10 | 6.38 (s) |
| 13 | 5.67 (t,7) |
| 14 | 2.64 (m) |
| 15 |  |
| 16 | 4.69 (s), 4.82 (s) |
| 17 | 1.62 (s) |
| 18 | 1.82 (s) |
| 19 | 1.53 (s) |
| 20 | 4.15 (ABq, 12 $V_{AB} = 55$) |
| 2' | 5.52 (d,2) |
| 3' | 6.02 (dd,2,9) |
| NH | 7.03 (d,9) |
| OAc | 1.85 (s), 2.00 (s), 2.13 (s), 2.17 (s), 2.22 (s) |
| 2-OBz | 7.93 (m), 7.2–7.9 (m)$^c$ |
| 3'-NBz | 7.85 (m) 7.2–7.9 (m)$^c$ |
| 3'-Ph | 7.2–7.9 (m)$^c$ |
| OH | 3.75 (s) |
| Other |  |

$^a$peak concealed under signals from methyl group
$^b$determined by decoupling experiment
$^c$overlapping peaks

EXAMPLE 7

The Meerwein product (4) was treated with acetyl chloride as follows: 50 mg of the Meerwein product (4) (0.057 mmol) was dissolved in CHCl$_3$; 3 mg pyrrolidinopyridine (an amount sufficient to catalyze the reaction) and excess acetyl chloride (5 eq) were added to the solution. Excess triethylamine was then added dropwise to the stirred solution at room temperature. A red color developed, which disappeared when more acetyl chloride was added; additional triethylamine and acetyl chloride were added until a single major product was obtained. The reaction was stopped after a total reaction time of 5 hours by addition of 3 ml of water and stirring for 30 minutes. Standard work-up was followed with an additional wash with 3N HCl. The mixture of products was subjected to PTLC to obtain the major component as 10 mg of a white solid (18%). $^1$H NMR, mass spectrometry, and infrared spectrometry confirmed that this compound was identical to the acetyl product of Example 6, acetylated A-Nor-D-seco-taxol (7)

EXAMPLE 8

The acetylated A-Nor-D-seco-taxol (7) was hydrogenated to its dihydro derivative (8) (FIG. 7) as follows: 24 mg of the acetyl chloride product (7) (0.023 mmol) was dissolved in 2.5 ml ethyl acetate, and hydrogenated over Pd/H$_2$. After 24 hours, the catalyst was filtered off, and the solvent was evaporated to yield a crude solid, which consisted of product and unreacted starting material; the unreacted starting material was not separable from the product. The crude product was dissolved in methylene chloride and treated with 5 mg m-chloroperbenzoic acid (58%) at room temperature for 3 hours; this converted the starting material to its separable epoxide. The solvent was evaporated and the residue subjected to PTLC with 44 MeOH/CHCl$_3$ to yield 8 mg pure hydrogenated product (8) (35%) along with 11 mg of a mixture of diastereomeric epoxides. The hydrogenated product (8) was recrystallized from ethyl acetate and hexanes. Characterization data is presented in Table I below and NMR data is presented in Table IX below.

TABLE IX

Characterization Data for Hydrogenated Acetylated A-Nor-D-Seco-Taxol (8)

| | |
|---|---|
| Melting Point | 148–150° C. |
| IR (KBr) cm$^{-1}$ | 1740(s), 1720(m), 1640(m), 1220(m), 910(m) |
| MS(FAB) m/z (relative intensity) | 1004(MNa$^+$, 100), 962(MNa$^+$—C$_3$H$_6$, 10), 944(MNa$^+$—HOAc, 15) |

TABLE X

NMR Data For Hydrogenated Acetylated A-Nor-D-Seco-Taxol (8)

| Carbon Position | $^1$H Shift (PPM from TMS) Coupling Hertz |
|---|---|
| 2 | 5.17 (d,8) |
| 3 | 3.68 (d,8) |
| 5 | 4.94 (br d, 11) |
| 6 | a |
| 7 | 5.54 (dd,5,11) |
| 10 | 6.36 (s) |
| 13 | 5.72 (m) |
| 14 | 2.48 (AB part of ABX, 14, 16  V$_{AB}$ = 65) |
| 15 | 1.60 (m) |
| 16 | 0.76 (d, 7) |
| 17 | 0.78 (d, 7) |
| 18 | 1.83 (s) |
| 19 | 1.53 (s) |
| 20 | 4.11 (ABq, 11  V$_{AB}$ = 78) |
| 2' | 5.40 (d,3) |
| 3' | 5.95 (dd,3,8) |
| NH | 7.02 (d,8) |
| OAc | 1.17 (s), 1.18 (s), 2.00 (s), 2.13 (s), 2.17 (s) |
| 2-OBz | 7.91 (m), 7.2–7.6 (m)$^c$ |
| 3'-NBz | 7.83 (m), 7.2–7.6 (m)$^c$ |
| 3'-Ph | 7.2–7.6 (m)$^c$ |

TABLE X-continued

NMR Data For Hydrogenated Acetylated A-Nor-D-Seco-Taxol (8)

| Carbon Position | $^1$H Shift (PPM from TMS) Coupling Hertz |
|---|---|
| OH | |
| Other | |

$^a$peak concealed under signals from methyl group
$^b$determined by decoupling experiment
$^c$overlapping peaks

EXAMPLE 9

Figure 6:
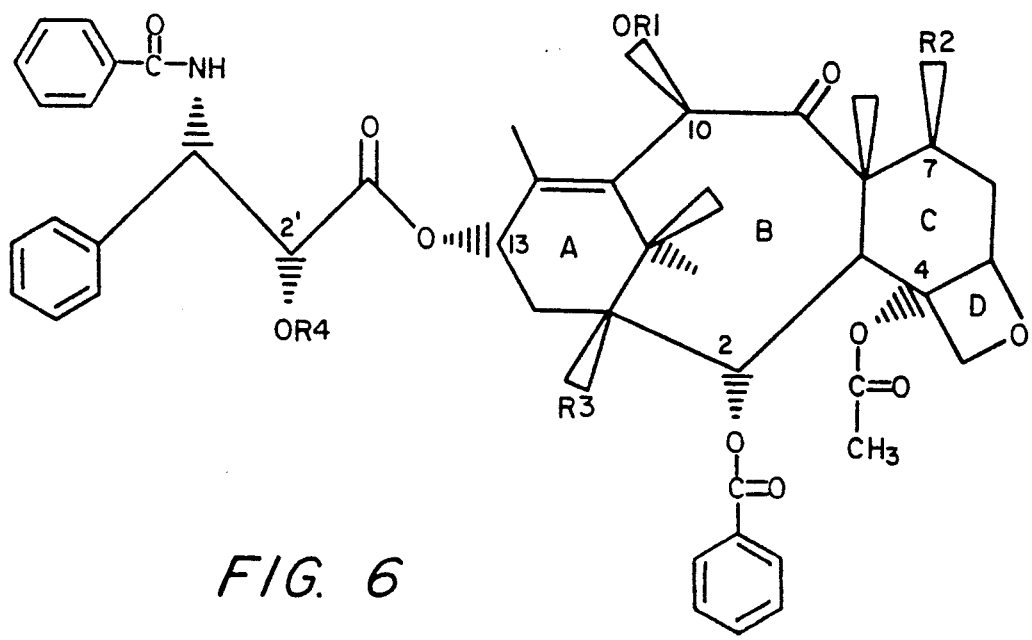
FIG. 6 is an alternate generalized representation of a taxol compound.
Figure 7:
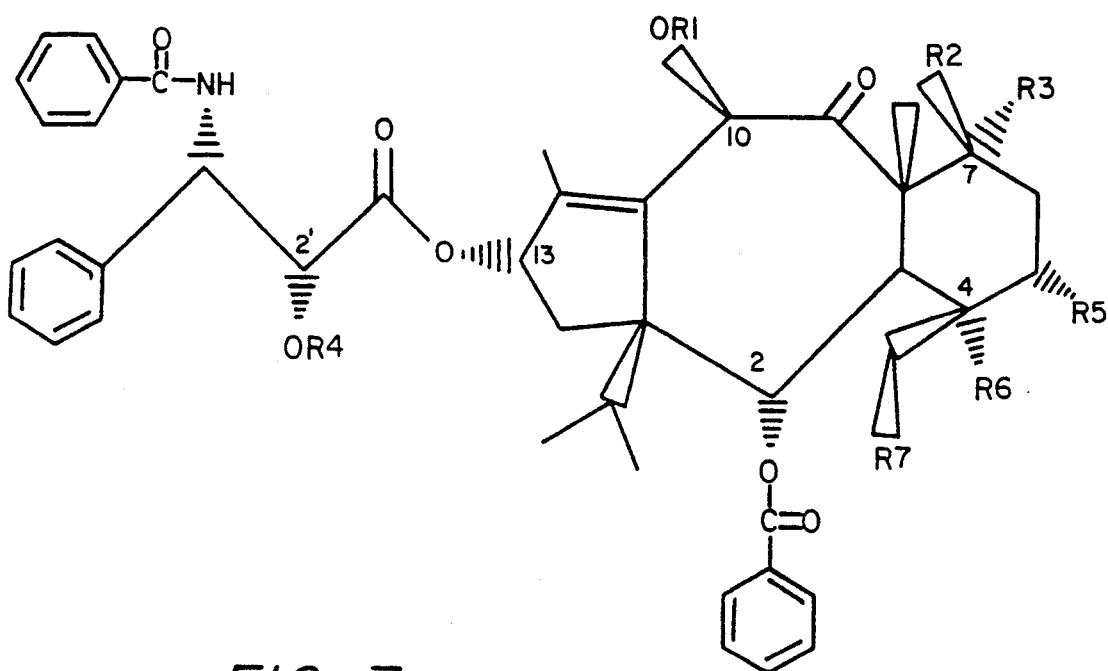
FIG. 7 is a generalized representation of the hydrogenated form of the compound illustrated in FIG. 3.

Taxol was reacted with imidazole and triethylsilylchloride as follows: 238 mg of solid imidazole (10 eq) was added to a solution of 200 mg taxol (0.234 mmol) in 2.5 ml DMF; 196 μl triethylsilylchloride (10 eq) was then added to the stirred solution while the solution was at room temperature, followed by warming the solution to 45°–500° C. After 2 hours, the solution was diluted with water, and extracted with ethyl acetate. The crude solid obtained after evaporation of the solvent was purified on a silica gel flash column to yield 242 mg (96%) of pure 2',7-bis (triethylsilyl)taxol (11) (FIG. 6). Characterization data is presented in Table XI and NMR data is presented in the Table XII below.

TABLE XI

Characterization Data For 2', 7-bis(triethylsilyl)taxol (11)

| | |
|---|---|
| Melting Point | 122–123° C. |
| IR cm$^{-1}$ | 1740(s), 1720(s), 1660(s), 1640(m), 1240(s), 810(m) |
| MS(FAB) m/z (relative intensity) | 1104(MNa$^+$, 100), 1003(30), 981(MNa$^+$—PhCOOH, 10) |

TABLE XII

NMR Data For 2', 7-bis(triethylsilyl)taxol (11)

| Carbon Position | $^1$H Shift (PPM from TMS) Coupling Hertz |
|---|---|
| 2 | 5.71 (m) |
| 3 | 3.88 (d,6) |
| 5 | 4.94 (br d, 11) |
| 6 | a |
| 7 | 4.48 (dd,6,14) |
| 10 | 6.44 (s) |
| 13 | 6.20 (m) |
| 14 | a |
| 15 | |
| 16 | 1.22 (s) |
| 17 | 1.18 (s) |
| 18 | 2.02 (s) |
| 19 | 1.70 (s) |
| 20 | 4.27 (ABq, 11  V$_{AB}$ = 63) |
| 2' | 4.71 (d, 3) |
| 3' | 5.71 (m) |
| NH | 7.12 (d,9) |
| OAc | 2.17 (s), 2.55 (s) |
| 2-OBz | 8.12 (m) 7.2–7.5 (m)$^c$ |
| 3'-NBz | 7.79 (m) 7.2–7.5 (m)$^c$ |
| 3'-Ph | 7.2–7.5 (m)$^c$ |
| OH | |
| Other | 0.48 (6H,m)$^c$ 0.57 (6H,m) 0.81 (9H,t,8) 0.91 (9H,t,8) |

$^a$peak concealed under signals from methyl group
$^b$determined by decoupling experiment
$^c$overlapping peaks

EXAMPLE 10

2',7-bis(triethylsilyl)taxol (11) was treated with triethylazine and mesyl chloride (methane sulfonyl chloride) as follows: 30 mg of 2',7-bis(triethylsilyl)taxol (11) (0.028 mmol) was added to 3 ml of dry methylene chloride, and cooled to $-15°$ C. under argon. 600 $\mu$l of triethylamine (154 eq) was added, followed by addition of 300 $\mu$l of mesyl chloride (138 eq) in 1 ml methylene chloride, with the additions made over a 5 minute period. The mixture was allowed to warm to $-5°$ to $0°$ C., and this temperature was maintained for a total reaction time of 2.5 hours, at which time 50% conversion of the starting material to 2',7-bis(triethylsilyl)-A-Nortaxol (9) (FIG. 4) was observed. The solution was cooled again to $-15°$ C., and 1 ml triethylamine and 500 $\mu$l mesyl chloride were added; this latter procedure was repeated one additional time. The reaction was then stopped by adding 2 ml triethylamine, 5 ml water, and 5 ml ethyl acetate. Standard work-up yielded crude material, which was purified by PTLC to give 6 mg (20%) of 2',7-bis(triethylsilyl)-A-Nor-taxol (9) (FIG. 4) along with 2 mg starting material and 2 mg 7-triethylsilyl-A-Nor-taxol. It is believed that the mesylate (13) (FIG. 6) is formed as an intermediate between (11) and (9). Mass spectrometry data, m/z, are as follows: 1086(MNa+, 45), 1064(MH+, 75), 1005(MH+—OAc, 25), 975(MH+—OAc—CH$_2$O, 15), 963(MH+—OAc—C$_3$H$_6$, 15), 820MH+—Ph-COOH,PhCONH$_2$—H, 100). NMR data is presented in Table XIII below:

TABLE XIII

NMR Data For 2', 7-bis(triethylsilyl)-A-Nor-taxol (9)

| Carbon Position | $^1$H Shift (PPM from TMS) Coupling Hertz |
|---|---|
| 2 | 5.54 (d,8) |
| 3 | 3.53 (d,8) |
| 5 | 5.02 (d,8) |
| 6 | 1.90 (m) |
| 7 | 4.53 (dd,8,5) |
| 10 | 6.39 (s) |
| 13 | 5.81 (br t,7) |
| 14 | 2.40 (m) |
|   | 2.60 (m) |
| 15 |   |
| 16 | 4.66 (s), 4.75 (s) |
| 17 | 1.65 (s) |
| 18 | 1.62 (s) |
| 19 | 1.73 (s) |
| 20 | 4.15 (ABq, 12) |
|    | V$_{AB}$ = 26) |
| 2' | 4.60 (d,2) |
| 3' | 5.64 (dd,2,11) |
| NH | 7.15 (d,11) |
| OAc | 2.02 (s), 2.40 (s) |
| 2-OBz | 8.01 (m) |
|       | 7.2–7.5 (m)$^c$ |
| 3'-NBz | 7.70 (m) |
|        | 7.2–7.5 (m)$^c$ |
| 3'-Ph | 7.2–7.5 (m)$^c$ |
| OH |   |
| Other | 0.38 (6H,m)$^e$ |
|       | 0.60 (6H,m) |
|       | 0.75 (9H,t, 8) |
|       | 0.90 (9H,t, 8) |

$^a$peak concealed under signals from methyl group
$^b$determined by decoupling experiment
$^c$overlapping peaks
$^e$signals of the ethyl groups of the TES groups

EXAMPLE 11

2',7-bis(triethylsilyl)-A-Nor-taxol (9) was treated with pyridinium hydrofluoride as follows: 67 ml 2',7-bis(triethylsilyl)-A-Nor-taxol (9) (0.07 mmol) was dissolved in 1 ml dry THF under argon. The solution was cooled to $0°$ C. and 100 $\mu$l pyridinium hydrofluoride (70% in pyridine) was added. After 3 hours the cooling bath was removed, and the reaction was allowed to proceed for an additional 45 hours at room temperature. The reaction was quenched with 2 ml aqueous pyridine (10% v/v pyridine). Standard work-up resulted in a crude solid which was purified by PTLC with 8% MeOH/CHCl$_3$, as the eluent. A-nor-taxol (10) was obtained as a white solid in 55% yield (29 mg). (Note that deprotection of the silyl ether (9) yielded a mixture of products when tetrabutylammonium fluoride was used instead of pyridinium hydrofluoride.) Mass spectrometry data, m/z (relative intensity), as follows: 836(MH+, 100), 776(MH+-HOAc, 30), 551(836-side-chain-H, 10), 307(20); High resolution mass spectrum calculated for C$_{47}$H$_{50}$NO$_{13}$(MH+) was 836.3282, observed 836.3272. $^1$H NMR i s presented in Table XIV below.

TABLE XIV $^1$H NMR Data For A-Nor-Taxol (10)

| Carbon Position | $^1$H Shift (PPM from TMS) Coupling Hertz |
|---|---|
| 2 | 5.49 (d,8) |
| 3 | 3.48 (d,8) |
| 5 | 5.04 (d,8) |
| 6 | 1.86 (dd,11,15); |
|   | 2.59 (ddd,8,9,15) |
| 7 | 4.63 (dd,9,11) |
| 10 | 6.32 (s) |
| 13 | 5.71 (m)$^c$ |
| 14 | 2.04 (dd,8,13) |
|    | 2.42 (dd,13,6) |
| 15 |   |
| 16 | 4.69 (br s) |
|    | 4.76 (br s) |
| 17 | 1.59 (s) |
| 18 | 1.61 (s) |
| 19 | 1.64 (s) |
| 20 | 4.24 (ABq, 8 |
|    | V$_{AB}$ = 34) |
| 2' | 4.67 (d,2) |
| 3' | 5.71 (dd,11,2)$^c$ |
| NH | 6.89 (d,11) |
| OAc | 2.17 (s), 2.36 (s) |
| 2-OBz | 8.10 (m) |
|       | 7.2–7.6 (m)$^c$ |
| 3'-NBz | 7.66 (m) |
|        | 7.2–7.6 (m)$^c$ |
| 3'-Ph | 7.2–7.6 (m)$^c$ |
| OH |   |
| Other |   |

$^a$peak concealed under signals from methyl group
$^b$determined by decoupling experiment
$^c$overlapping peaks

BIOLOGICAL TESTING OF TAXOL DERIVATIVES

Taxol (1), the Meerwein product (4), the acetyl chloride product (7), and A-nor-taxol (10) were tested in KB cell culture assays. All of the samples showed in vivo activity as shown in Table XV below (note that an ED$_{50}$($\mu$g/ml) of less than 4.0 indicates in vivo activity). Taxol has been shown to have great potential as an anti-cancer drug, so that these compounds can be used in a similar fashion to taxol as cytotoxic agents.

TABLE XV

Bioactivity of Modified Taxols In KB Cell Culture

| Compound | ED$^{50}$ ($\mu$g/ml) cell culture |
|---|---|
| Taxol (1) | 0.00001 |
| Meerwein product (4) | 2.3 |
| Acetyl Chloride product (7) | 2.5 |

TABLE XV-continued

| Bioactivity of Modified Taxols In KB Cell Culture | |
|---|---|
| Compound | $ED^{50}$ (μg/ml) cell culture |
| A-Nortaxol (10) | 2.0 |

Taxol (1), the Meerwein product (4), the acetyl chloride product (7), and A-Nor-Taxol (10) were also subjected to tubulin depolymerization assays with the results presented in Table XVI below.

TABLE XVI

| In Vitro Activity In Tubulin Depolymerization Assay | |
|---|---|
| Compound | $ID_{50}$ (μM) in tubulin depolymerization assay |
| Taxol (1) | 0.3 |
| Meerwein product (4) | >6.3 |
| A-Nortaxol (10) | 0.9 |

Note that A-Nor-Taxol (10) has an activity which is very similar to taxol in the tubulin depolymerization assay. Since the A-Nor-Taxol (10) structure has a fused A-ring, A-Nor-Taxol (10) is a more likely candidate for total synthesis than taxol. Further, because A-Nor-taxol has been found to be cytotoxic, and to have an in vitro activity close to taxol's in a tubulin depolymerization assay, it is believed that A-Nor-taxol (10) may have bioactivity mechanisms very similar to taxol's (1).

With reference to Table XV, note that the in vivo activity of A-Nor-Taxol (10), the Meerwein product (4), and the acetyl chloride product (7) are 2.0, 2.3, and 2.5 respectively. This range of in vivo activities makes these compounds useful as standards for testing other compounds, eliminating the need for taxol standards. Since, the relative in vivo activity of these compounds is now known, the bioactivity of an unknown compound can be determined with respect to these compounds without having to refer to any published data or without use of taxol as a standard.

A preferred process for testing the bioactivity of unknown compounds, or for testing taxol-derived pharmaceuticals, includes treatment of an unknown sample in a bioactivity test, and simultaneous treatment under the same conditions of at least one, preferably of all three, of the following products: A-Nor-Taxol. (10), the Meerwein product (4), and the acetyl chloride product (7). By comparison of results for the unknown sample with the results for the products (4), (7), and (10), the in vivo activity of the unknown can be determined.

Due to the bioactivity demonstrated for some of the compounds of the present invention, it is believed that compounds (4)-(12) will be useful directly as, or as intermediates for, antineoplastic, antileukenic and anticancer prodrugs or drugs, and their use as such is considered to be a part of the present invention.

Contemplated equivalents of the rearranged taxol compounds of the present invention include rearranged taxol compounds having a contracted A-ring, an opened oxetane ring, or a contracted A-ring and an opened oxetane ring, which have one or more side chain or ring substituents substituted with a non-interfering group (e.g., a substituted group which does not seriously alter the desirable properties of the rearranged taxol compounds of the present invention), such as, but not limited to, substitution of —H, —OH, —OR, —NR, —Ar, —OC(O)CH₃, Ph—O—, Ph—N—, or =O for another non-interfering moiety.

From the above teachings, it is apparent that many modifications and variations of the present invention are possible. It is therefore to be understood that the invention may be practiced otherwise than as specifically described.

We claim:

1. A taxol compound having the following structure:

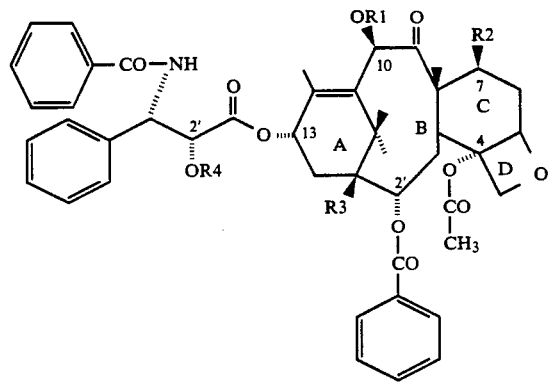

wherein R1 is C(O)CH₃, R2 is OH or OSi(CH₂CH₃)₃, R3 is OSO₂CH₃, and R4 is H or Si(CH₂CH₃)₃.

2. A process for producing rearranged taxol compounds, comprising the reaction of taxol with an oxonium compound to form a taxol compound with an opened oxetane ring; and reacting said taxol compound with an opened oxetane ring with dimethoxypropane in the presence of p-toluenesulfonic acid.

3. The process of claim 2, wherein said oxonium compound is triethyloxonium tetrafluoroborate.

* * * * *